(12) United States Patent
Rashidi et al.

(10) Patent No.: US 9,730,812 B2
(45) Date of Patent: Aug. 15, 2017

(54) ADJUSTABLE TESTING APPARATUS FOR AN ORTHOPAEDIC SPECIMEN SUCH AS A KNEE IMPLANT PROSTHESIS

(71) Applicant: ORTHOPAEDIC RESEARCH LABORATORIES, Cleveland, OH (US)

(72) Inventors: Majid Rashidi, Pepper Pike, OH (US); Alon Katz, Decatur, GA (US); Paul D. Postak, University Heights, OH (US); A. Seth Greenwald, Cleveland Heights, OH (US)

(73) Assignee: ORTHOPAEDIC RESEARCH LABORATORIES, Cleveland, OH (US)

( * ) Notice: Subject to any disclaimer, the term of this patent is extended or adjusted under 35 U.S.C. 154(b) by 0 days.

(21) Appl. No.: 15/045,530

(22) Filed: Feb. 17, 2016

(65) Prior Publication Data

US 2016/0235550 A1   Aug. 18, 2016

Related U.S. Application Data

(63) Continuation-in-part of application No. 13/841,645, filed on Mar. 15, 2013, now Pat. No. 9,402,750.

(51) Int. Cl.
*G01B 5/30* (2006.01)
*A61F 2/46* (2006.01)
*A61F 2/38* (2006.01)
*A61F 2/76* (2006.01)

(52) U.S. Cl.
CPC .............. *A61F 2/468* (2013.01); *A61F 2/38* (2013.01); *A61F 2/76* (2013.01)

(58) Field of Classification Search
CPC .... A61F 2/468; A61F 2/24; A61F 2/38; A61F 2/3859; A61F 2/40; A61F 2/44; A61F 2/32; A61F 2/3804; A61F 2/389; A61F 2/4202; A61F 2/76
USPC .......................................... 73/804, 760, 818
See application file for complete search history.

(56) References Cited

U.S. PATENT DOCUMENTS 7,493,828 B2   2/2009 Greenwald et al.
7,823,460 B2   11/2010 White

*Primary Examiner* — Harshad R Patel
*Assistant Examiner* — Brandi Hopkins
(74) *Attorney, Agent, or Firm* — Fay Sharpe LLP

(57) ABSTRACT

A testing apparatus for exposing an associated specimen(s) to motions along multiple axes is provided. The testing apparatus includes a test chamber and first, second, third, and fourth devices that impose different kinematic motions or forces on the specimen. A drive mechanism is connected to the first, second, third, and fourth devices so that motion from a single axis is conveyed by the first, second, third and fourth devices to deliver the desired kinematic motions and/or forces to the test chamber(s). At least one of the first, second, third, and fourth devices includes an adjustment mechanism to modify at least one of the devices.

20 Claims, 19 Drawing Sheets

ADJUSTABLE TESTING APPARATUS FOR AN ORTHOPAEDIC SPECIMEN SUCH AS A KNEE IMPLANT PROSTHESIS

This continuation-in-part application claims the priority benefit of co-pending U.S. application Ser. No. 13/841,645, filed Mar. 15, 2013, the disclosure of which is expressly incorporated herein in its entirety.

BACKGROUND OF THE DISCLOSURE

This disclosure relates to a testing apparatus for orthopaedic specimens. In particular, this disclosure relates to a testing apparatus that is used to apply motions and forces to a test specimen(s) in a manner representative of what a prosthesis may encounter when implanted.

Various suppliers design and manufacture orthopaedic specimens in an effort to evaluate the suitability of a particular design for use such as a prosthesis, for example, a knee implant. Before these new designs are available for use, specimens must undergo rigorous testing under prescribed conditions. For example, ISO 14243 is a standard that sets forth criteria for evaluating the design and materials of knee implants, and particularly aids in evaluating the wear of test specimens. Imposed forces result in defined, discrete motions and the motions are coordinated with one another in a preselected environment (e.g., a force(s) applied in a particular pattern, for a desired time, at a desired velocity, and in a particular environment). The test is typically conducted for millions of cycles, for example, 5,000,000 to 10,000,000 cycles at 1 Hz. The test is extensive, carefully controlled, and test conditions are closely monitored, and preferably the testing apparatus can simultaneously test multiple, individual specimens under similar conditions.

For example, with reference to a knee implant and the noted ISO standard, a first defined action or motion ($e_y$) caused by the moment ($M_y$) is generally referred to as flexion/extension and relates to rotation about one axis of an orthogonal coordinate system. The driving force or torque, to achieve this motion is applied to the specimen, and particularly the femoral component of the test specimen, while the other component is representative of the tibia.

A second defined action or motion ($e_z$) caused by the moment ($M_z$) is rotation about one of the axes of the orthogonal coordinate system. This movement is representative of the movement of the tibia.

A third action or motion (X) caused by the force ($F_x$) is referred to as linear translation along one of the axes of the orthogonal coordinate system. In other words, this relates to forces that result in forward and backward motion imposed on the test specimen.

A fourth action relates to an axial compressive force ($F_z$) imposed on the test specimen. This axial force can rapidly increase in a short period of time. For example, a dynamic compressive load can rapidly increase by 1800 N in 0.03 seconds. Further, the dynamic load must be able to exceed a force of 2600 N.

These actions, i.e., motions and forces, must be controlled or synchronized. At least three of the forces/motions/actions are periodic. Further, the testing system must maintain this synchronized action on multiple specimens over an extended period of time (e.g. testing of multiple specimens through millions of cycles takes a few months to complete).

Conventional, commercially available systems use multiple electrohydraulic actuators to achieve the various motions and load magnitudes required under the ISO standard. Unfortunately, these electrohydraulic actuators are relatively expensive. Further, the electrohydraulic actuators are not particularly effective in measuring smaller forces (e.g. on the order of less than 70 N) nor do the electrohydraulic actuators have good resolution. Also, use of the electrohydraulic actuators and associated controls require expensive sensors in an effort to achieve coordinated synchronization or phased movement as required under the ISO standard. As a result, the use of multiple electrohydraulic actuators, and the associated sensors and controls for the actuators, results in a test apparatus that is unduly expensive. These problems are magnified when the test apparatus is designed to simultaneously test multiple test specimens.

In other instances, it may be desirable to easily and effectively alter the force and/or motion imposed on a test specimen.

Accordingly, a need exists for an alternate test apparatus that is dependable, durable, accurate, easy-to-use, economical to manufacture and use, able to be altered, and can be easily adapted to multiple stations to permit simultaneous testing of multiple specimens.

SUMMARY OF THE DISCLOSURE

An improved testing apparatus exposes an associated specimen to forces and motions along and about multiple axes. The testing apparatus includes a test chamber dimensioned to receive the associated specimen. A drive mechanism is connected to first, second, third, and fourth devices so that the forces/motions imposed on the associated test specimen are preferably commonly driven. At least one of the first, second, third, and fourth devices includes an adjustment mechanism to modify at least one of the devices.

In one preferred arrangement, a first device imposes a first, rotational movement on the associated specimen. A second device imposes a second, rotational movement different than the first rotational movement, on the associated specimen. A third device imposes a generally linear translation on the associated specimen. A fourth device imposes a dynamic force on the associated specimen.

The first device is preferably configured to rotate the associated specimen about a first axis, while the second device is preferably configured to rotate the associated specimen about a second axis, and more preferably about a second axis orthogonal to the first axis.

The third device is preferably configured to apply linear translation to the associated specimen, while the fourth device is preferably configured to impose a periodic, dynamic, compressive force on the associated specimen.

The drive mechanism preferably includes first and second cams that are configured to rotate together, and in one preferred embodiment the first and second cams are generally annularly shaped to provide first, second, third, and fourth cam profiles.

Associated first, second, third, and fourth followers each operatively engage one of the first and second cams, and in a preferred arrangement, each of the followers engages one of the profiles.

Each of the first, second, third, and fourth devices includes a restoring member configured to urge the first, second, third, and fourth followers against one of the first and second cams, and preferably urges one of the followers against one of the profiles.

A method of testing the specimen includes placing the specimen in a test chamber, imposing a dynamic, compressive force on the specimen, providing a substantially linear translation on the specimen about one of the axes, applying rotational motions about the other two orthogonal axes, and commonly driving the force, linear translation, and the two rotations with a drive mechanism, and the method may include adjusting at least one of these actions (forces and/or motions).

The force imposing step includes applying a dynamic, periodic, compressive force on the specimen.

The commonly driving step includes rotating first and second cams together.

The method further includes providing first, second, third, and fourth followers that engage at least one of the first and second cams.

The driving step preferably includes providing first and second generally annular cams rotated about a single axis where each cam has an inner and outer profile and each profile is engaged by at least one of first, second, third, and fourth followers.

The method further includes urging each of the first, second, third, and fourth followers against a respective profile.

The method may also include assembling multiple testing apparatus together in a coordinated configuration in order to simultaneously test multiple, individual specimens under the same conditions.

The assembly of multiple testing apparatus is preferably commonly driven by the same drive mechanism, preferably the first and second cams.

A primary advantage of the disclosure relates to eliminating use of electrohydraulic actuators (and associated controls and sensors) in the testing apparatus.

Another benefit of the disclosure is the preparation of a testing apparatus that is dependable, durable, and accurate.

Still another advantage relates to the ability to easily replicate multiple testing apparatus into a multiple station system.

Yet another benefit resides in the reduced cost to manufacture a reliable system.

Still other benefits and advantages will become apparent to those skilled in the art upon reading and understanding the following detailed description.

DETAILED DESCRIPTION OF THE PREFERRED EMBODIMENT

Figure 1:
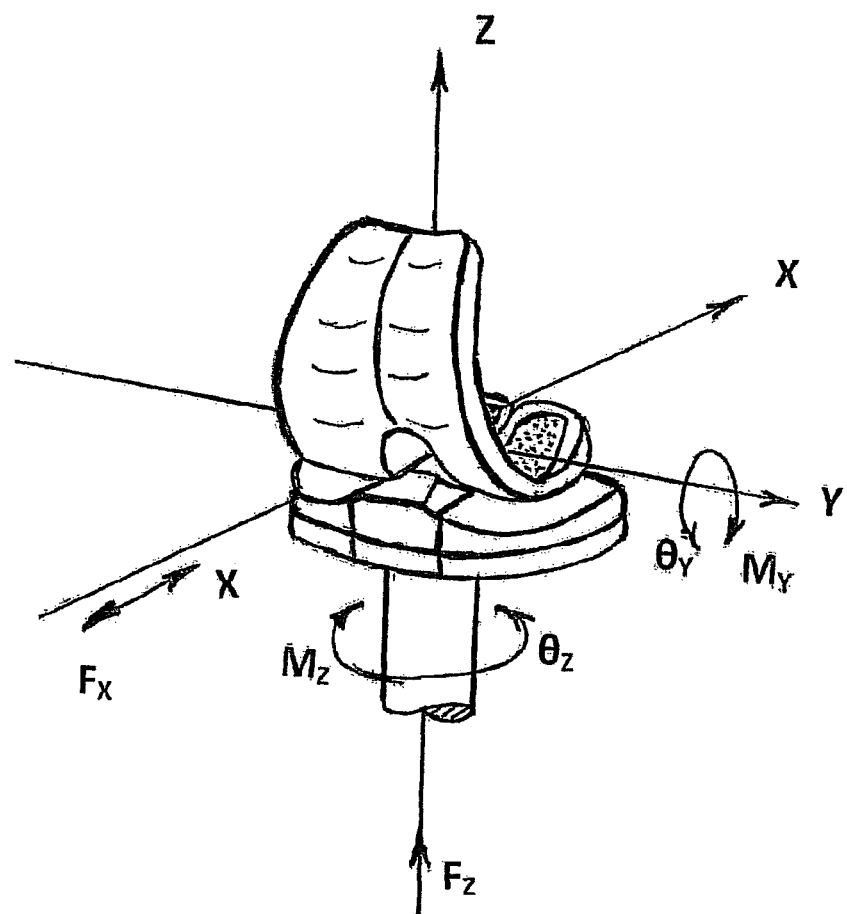
FIG. 1 defines the orthogonal coordinate system and the forces/motions.
Figure 2:
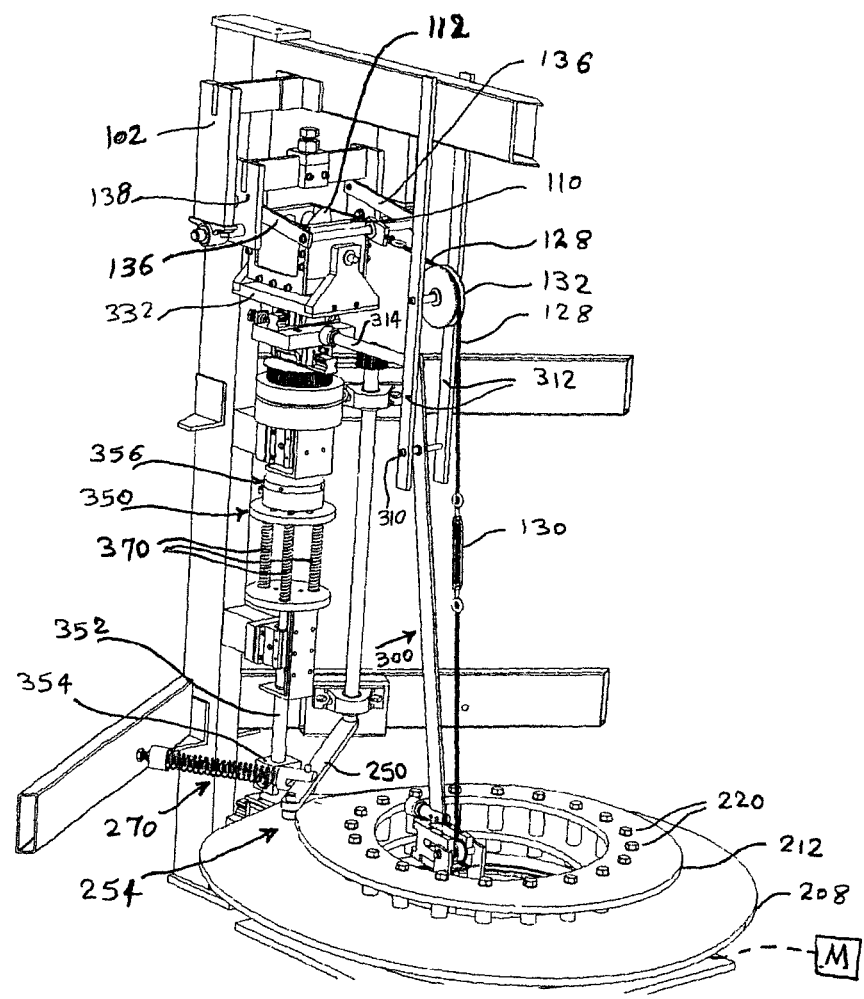
FIG. 2 is a perspective view of a testing apparatus.

The machine described herein produces three kinematic motions and a dynamic force along the three axes of an orthogonal coordinate system which is fixed in space with its origin located within the specimen. FIG. 1 depicts the set of orthogonal system axes with the kinematic motions and dynamic force schematically shown. For example, the first kinematic motion [$e_y$] is rotation about the first axis of the orthogonal coordinates which is produced by the moment $M_y$. The second kinematic motion [$e_z$] is rotation about the second axis produced by the moment $M_z$. The dynamic force $F_z$ acts along the same axis. The third kinematic motion is linear translation [X] which takes place along the third axis in response to the force $F_x$. FIG. 2 shows a testing apparatus 100 supported by a frame 102 that includes a test chamber 110 for receiving an associated test specimen 112. The test chamber 110 is preferably configured so that the lower portion of test specimen 112 when mounted therein does not move relative to the test chamber. The test chamber 110 has a sealed cavity to receive a fluid at a predetermined temperature and that also meets other parameters specified by the testing protocol. The fluid serves as a medium having some characteristics comparable to those experienced in a human body. For example, if the test specimen is ultimately intended for use as an artificial knee implant, then the specimen will be immersed in the fluid and maintained at a temperature that is representative of the human body.

When mounted in the test chamber, selected forces and motions are imposed on the test chamber and consequently on the associated specimen. With initial reference to FIGS. 2 and 3 (and additionally FIGS. 4-6), the preferred testing apparatus 100 includes a first device 120 that is operatively connected to the test chamber to direct a first force that is configured relative to the test chamber to impose a rotational motion on the test specimen. The first device 120 preferably includes an elongated flexible member such as a cable or wire 122 having a first or lower end 124 secured to a first follower 126 and a second or upper end 128 operatively interconnected with a rotational mechanism to be described in greater detail below. Intermediate the first and second ends 124, 128, the cable 122 includes an adjustment device such as a turnbuckle 130 to maintain proper tension in the cable and assure that movement at the first end 124 is transferred to the second end 128. In addition, a pulley 132 is preferably disposed adjacent the test chamber 110 and is rotatably supported by a portion of the frame 102. The pulley 132 allows the first end of the cable to be located at a remote position relative to the test chamber, and yet effectively transfers vertical movement of the cable into generally horizontal motion of arm 134 extends between link arms 136. The link arms 136, in turn, are pivotally mounted at their opposite ends to respective support arms 138 that are disposed in generally parallel relation. The support arms 138 are mounted on opposite sides of the test chamber so that reciprocating motion of the second end 128 of the cable is translated into a rocking or limited arcuate motion of the test chamber 110. In this preferred arrangement, the arcuate motion is about a horizontal axis defined by pivotal mounting rod 140. Each end of the rod 140 is received in an elastomeric type material (e.g., rubber) 142 provided at each end of the rod and that is received over ends of parallel plates 144. The plates 144 are rigidly secured to the frame 102. The elastomeric material 142 is compressed when the test chamber is moved through an arc, and thus the elastomeric material 142 and the tension imposed by the turnbuckle 130 together serve as a restoring member configured to urge the first device 120 toward an at rest position.

Figure 4:
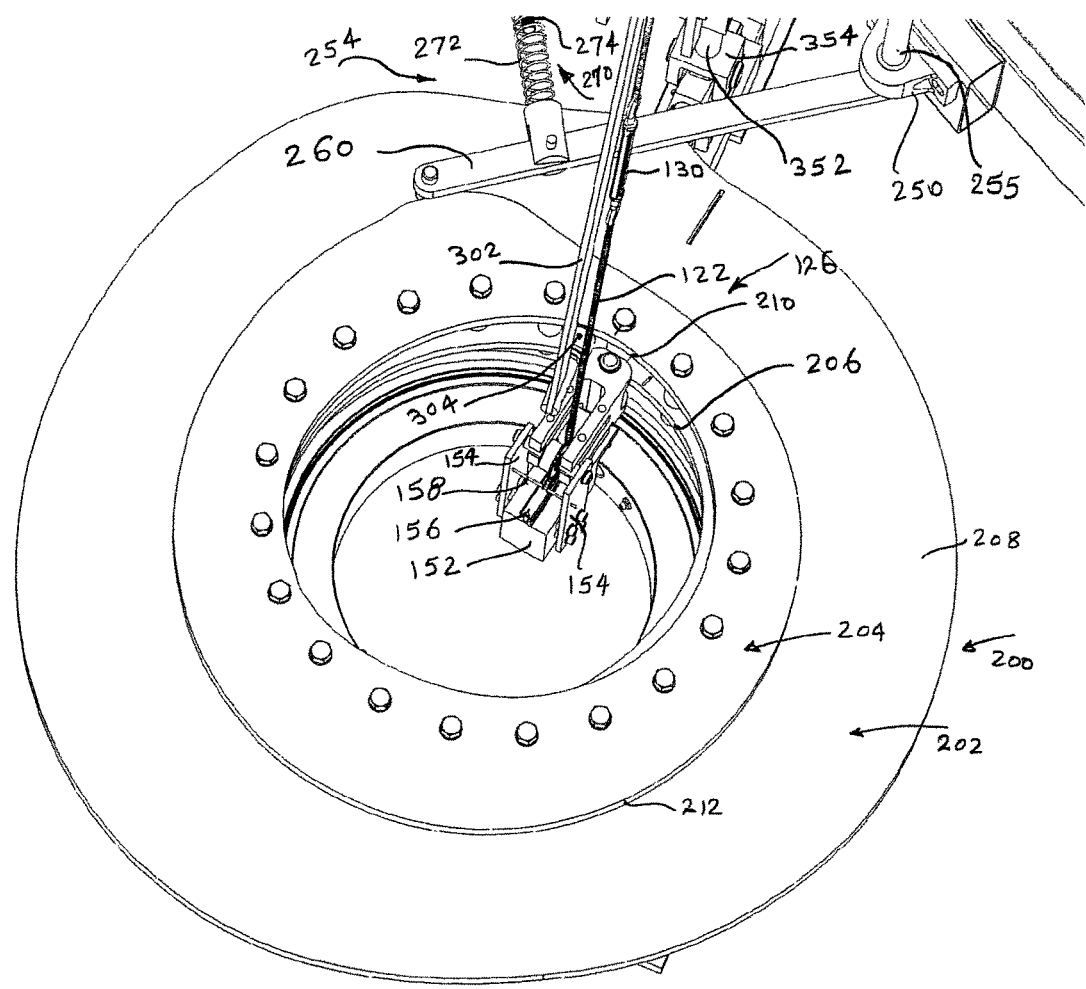
FIG. 4 is an enlarged perspective of inner surface profiles of the first and second cams.
Figure 5:
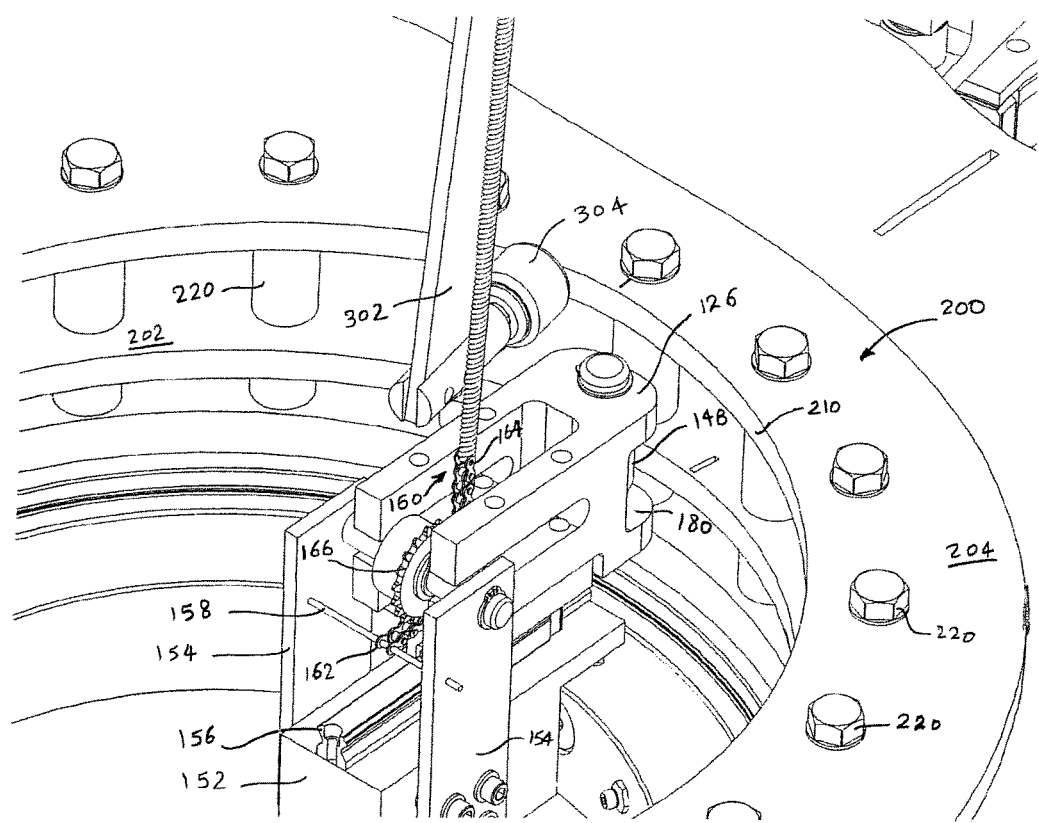
FIG. 5 is a further enlarged perspective of the inner surface profiles of the first and second cams.

The first end 124 of the cable is secured to the first follower 126 (FIGS. 4-5). More specifically, the first follower 126 is an assembly that includes a mount 152 secured to a portion of the frame 102 and having first and second members or mounting plates 154 extending upwardly from opposite sides of the mount. A track or keyway 156 is secured, for example, to an upper surface of the mount 152 at a location between the mounting plates and the track extends in a substantially radial direction. Extending between the mounting plates 154 at a location spaced above the track is a cross member or rod 158. A flexible member such as chain 160 is secured at a first end 162 to the rod 158. The chain 160 continues to a second end 164 that is secured or fixed to the lower end 124 of the cable 122. The chain 160 is partially wrapped about a toothed gear 166 that is rotatably supported for rotation about a horizontal axis by the mounting plates 154. The first follower 126 further includes a slide 180 that moves along the track 156 and includes a channel or groove 182 that together with the track 156 limits movement of a follower surface 184 so that the first follower travels in a generally radial direction and against at least a portion of a drive mechanism or rotary driver 200.

More particularly, the drive mechanism 200 (FIGS. 2-7) includes a first cam 202 and a second cam 204 that are driven by a drive motor M (schematically represented in FIG. 2) for rotation about a vertical axis relative to the frame 102. As illustrated in the drawings, each of the first and second cams 202, 204 is generally annularly shaped and are operatively engaged by followers. More particularly, the first annular cam 202 has a first or inner profile 206 and a second or outer profile 208 (FIG. 4). Likewise, the second cam 204 has a first or inner profile 210 and a second or outer profile 212. The cams 202, 204 are secured together for rotation about a common central or vertical axis. Fasteners such as bolts 220 extend between the annularly shaped cam plates 202, 204 to secure the cam plates together and assure that the cam plates rotate in unison. It is also evident that in this preferred arrangement, the first cam 202 has a larger, outer profile surface 208 than the outer profile 212 of the second cam. On the other hand, the inner profiles 206, 210, of the first and second cams, respectively, have approximately the same inner dimension. It will be appreciated though that the profiles, i.e., the arc or segmented portions that define the circumferentially continuous, inner annular surface or outer annular surface of each cam, may be different depending on the required movements of the followers that track along the surfaces of the profiles in order to translate to desired forces or motions imposed on the test chamber 110.

Thus, the first device 120 imposes a first, rotational motion ($e_y$) on the test chamber 110 or associated specimen 112 as the first cam 202 rotates. The first follower assembly 126, and more particularly surface 184, rides along the first profile 206 of the first cam 202. As the cam profile 206 increases or decreases in radial dimension, the guide 180 which is urged against the cam profile likewise moves radially inward and outward along track 156 thereby resulting in rotation of toothed gear 166 so that the cable 120 moves upwardly and downwardly between the first end 124 and the pulley 132, and the cable moves generally radially between the pulley 132 and the test chamber 110. The ordinarily skilled artisan will appreciate that the mechanical details of a first device that also achieves the same function may differ from that shown and described in the illustrated embodiment; however, the mechanical nature of the first mechanism is advantageously robust, reliable, accurate, inexpensive, etc. and easily synchronized with the other motion producing devices as will become apparent below.

A second device 250 (FIGS. 2-4, 6-8 and 11) is operatively connected to the test chamber 110 and imposes a second, rotational motion on the test chamber or associated specimen. More particularly, this rotational movement is generally defined herein as a rotation about a second axis that results in motion ($e_z$) of the test chamber 110. Here, the second device 250 preferably cooperates with the outer profile 212 of the second cam 204. One skilled in the art will appreciate, however, that the particular selected profile of the first or second cam is not critical, as long as the profile has a shape or conformation that meets the desired parameters of the test protocol. The second device 250 includes an elongated, vertical rod 252 that is operatively connected to a second follower 254 at a first or lower end and includes a drive member or toothed gear 256 at a second or upper end. The second follower 254 includes an arm 260 fixed to the first end of the elongated rod 252 at one end. A roller 262 is provided at a second end of the arm 260 that engages or rides along outer profile 212 of the second cam 204.

A restoring member 270 urges the roller 262 of the second follower 254 against the profile 212. In the illustrated embodiment, the restoring member 270 includes a spring 272 received around a guide member 274 extending outwardly from the frame 102. The other end of the spring 272 is operatively connected to the follower arm 260. As the roller 262 moves radially inward and outward in response to rotation of the cam assembly, the follower arm 260 pivots through a limited arc about the vertical axis defined by the elongated rod 252 of the second drive. Likewise, gear 256 at the upper end of the rod 252 drives a driven gear 280 that is operatively connected to the test chamber 110. The driving engagement between the drive gear 256 and a driven gear 280 is provided via a belt or similar flexible member (represented by dashed line in FIG. 11 but not shown in solid line for ease of illustration). Again, one skilled in the art will appreciate that the mechanical details of a second mechanism that also achieves the same function may differ from that shown and described in the illustrated embodiment; however, the mechanical nature of the second mechanism is advantageously robust, reliable, accurate, inexpensive, etc. and easily synchronized with the other motion producing devices.

Figure 3:
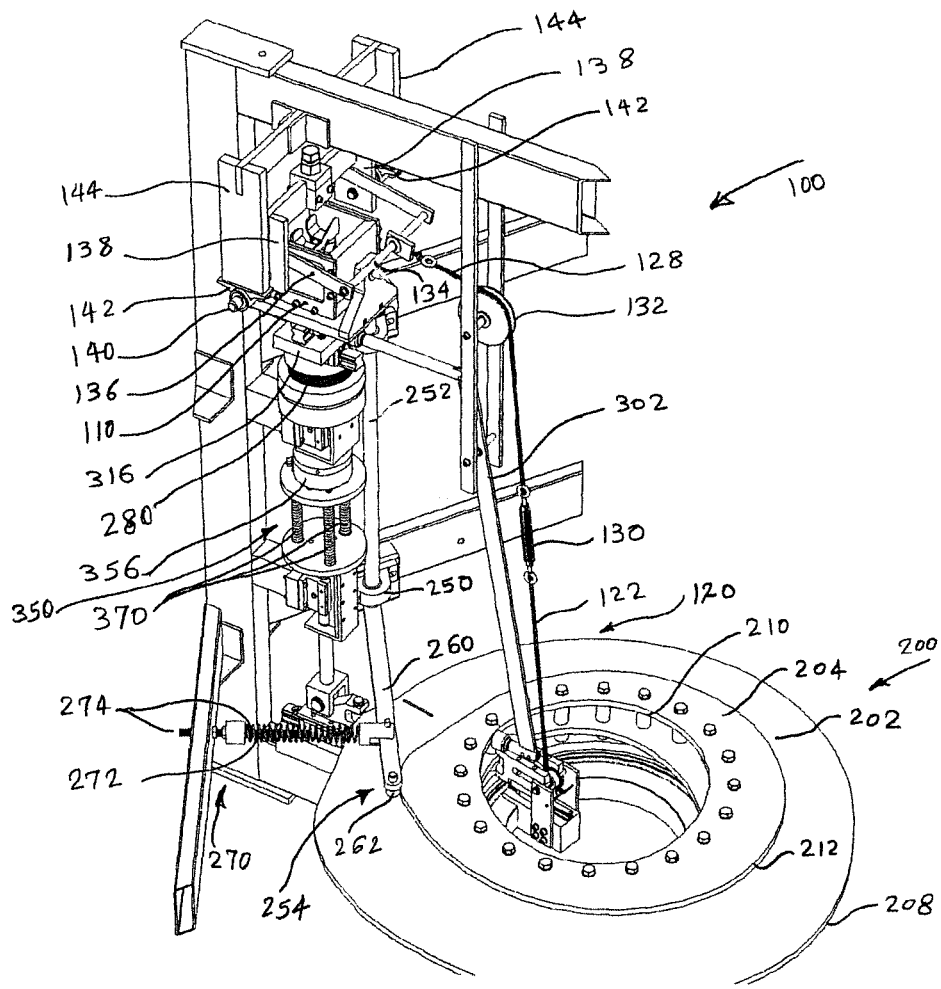
FIG. 3 is a perspective view of a testing apparatus of FIG. 2.
Figure 6:
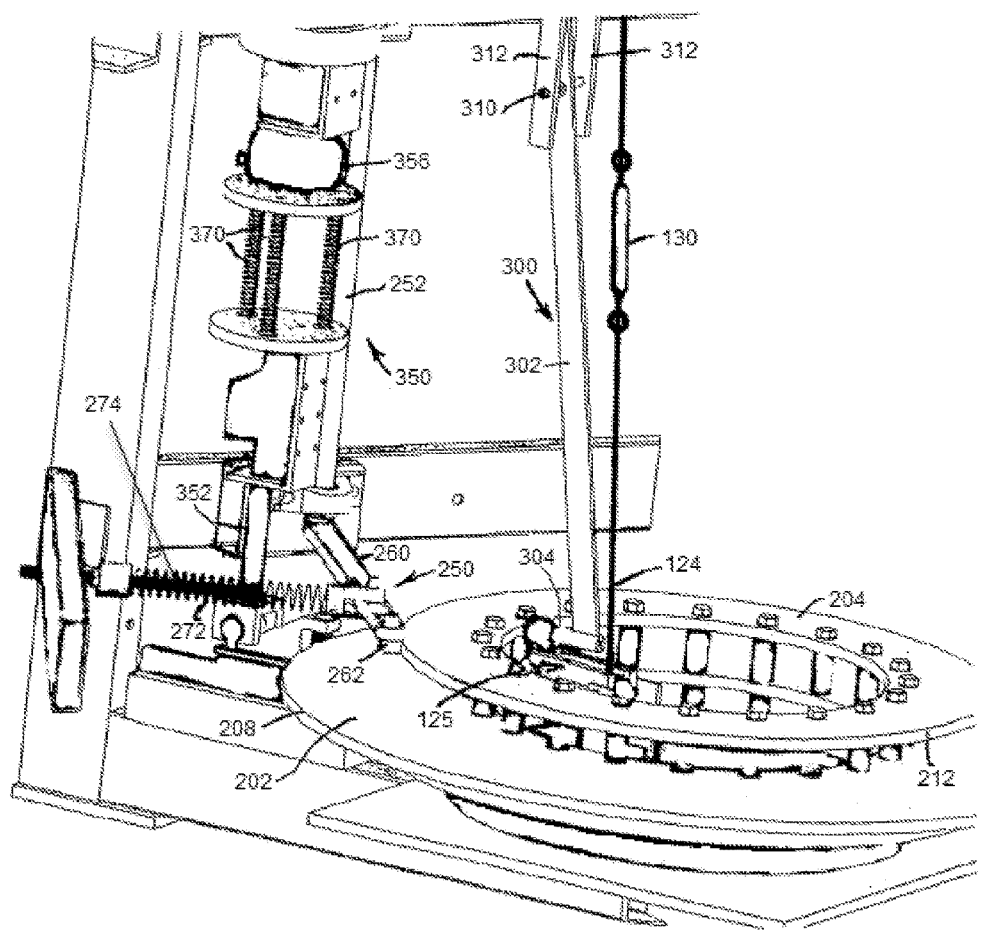
FIG. 6 is an enlarged perspective of the outer surface profiles of the first and second cams.
Figure 7:
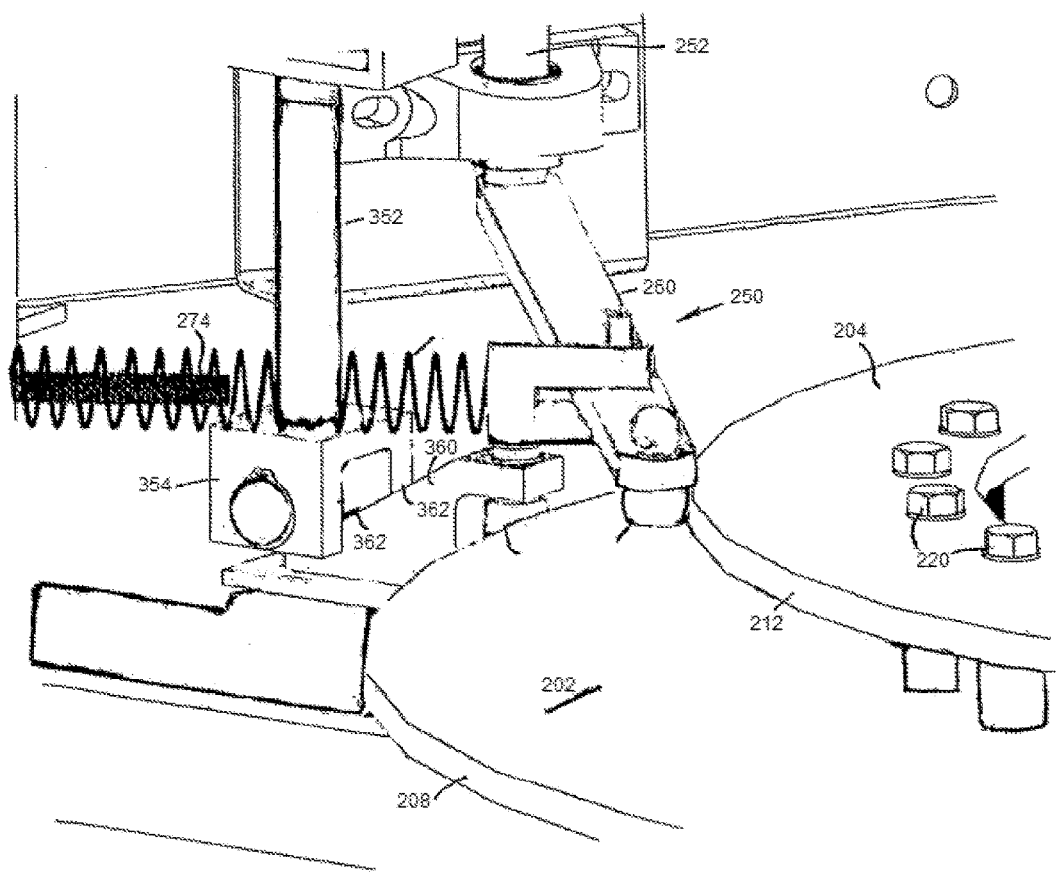
FIG. 7 is a further enlarged perspective view of the outer surface profiles of the first and second cams.
Figure 8:
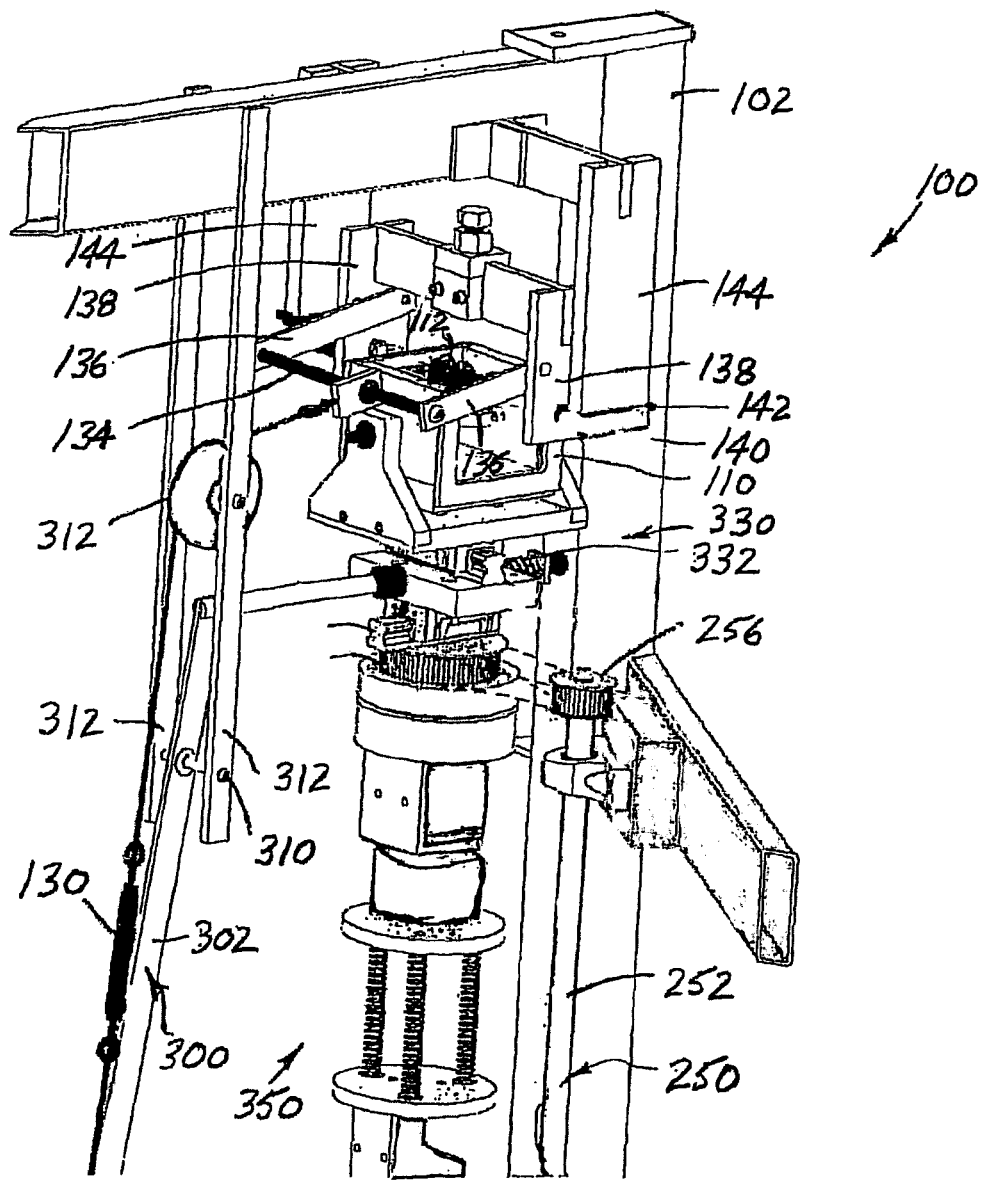
FIG. 8 is a perspective view of test chamber and the four forces/motions imposed thereon.
Figure 9:
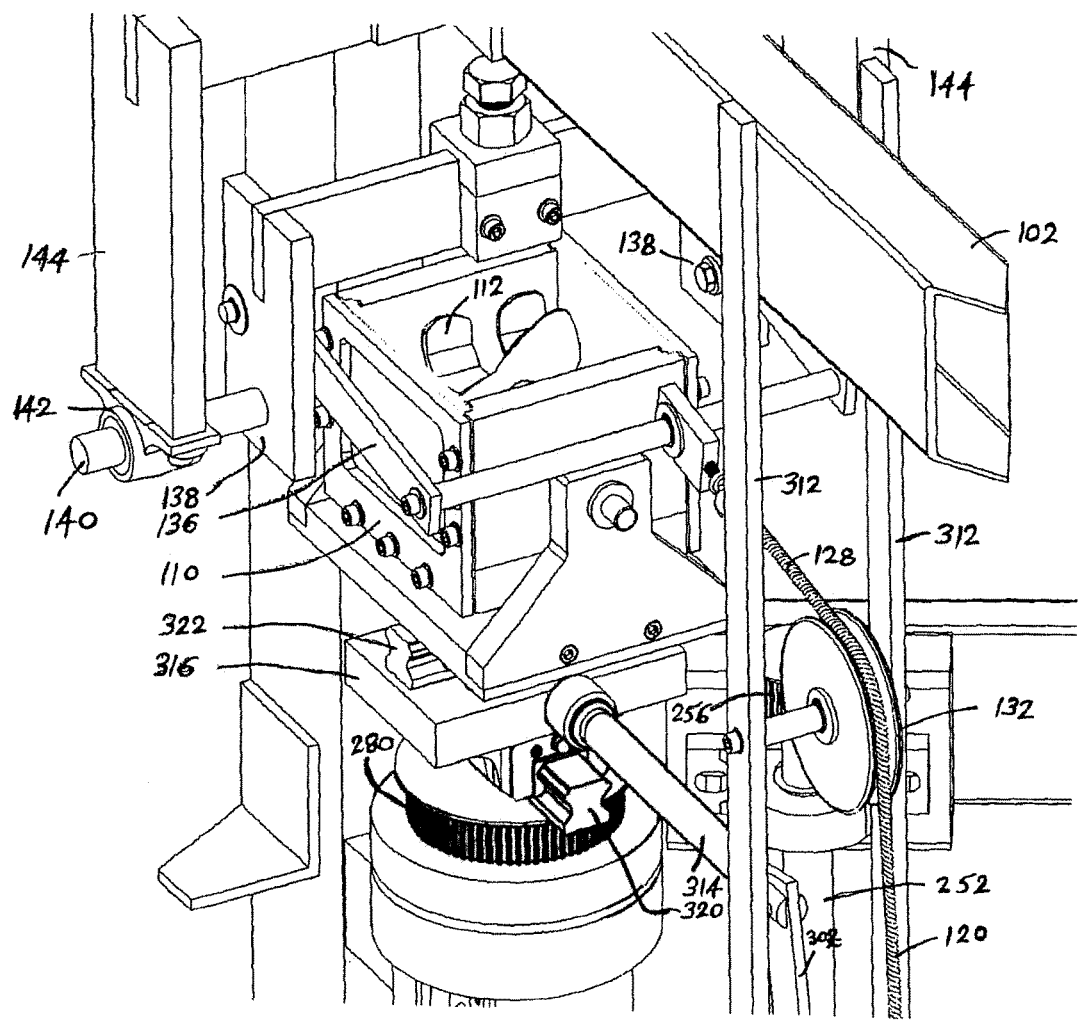
FIG. 9 is an enlarged perspective view of the test chamber.
Figure 10:
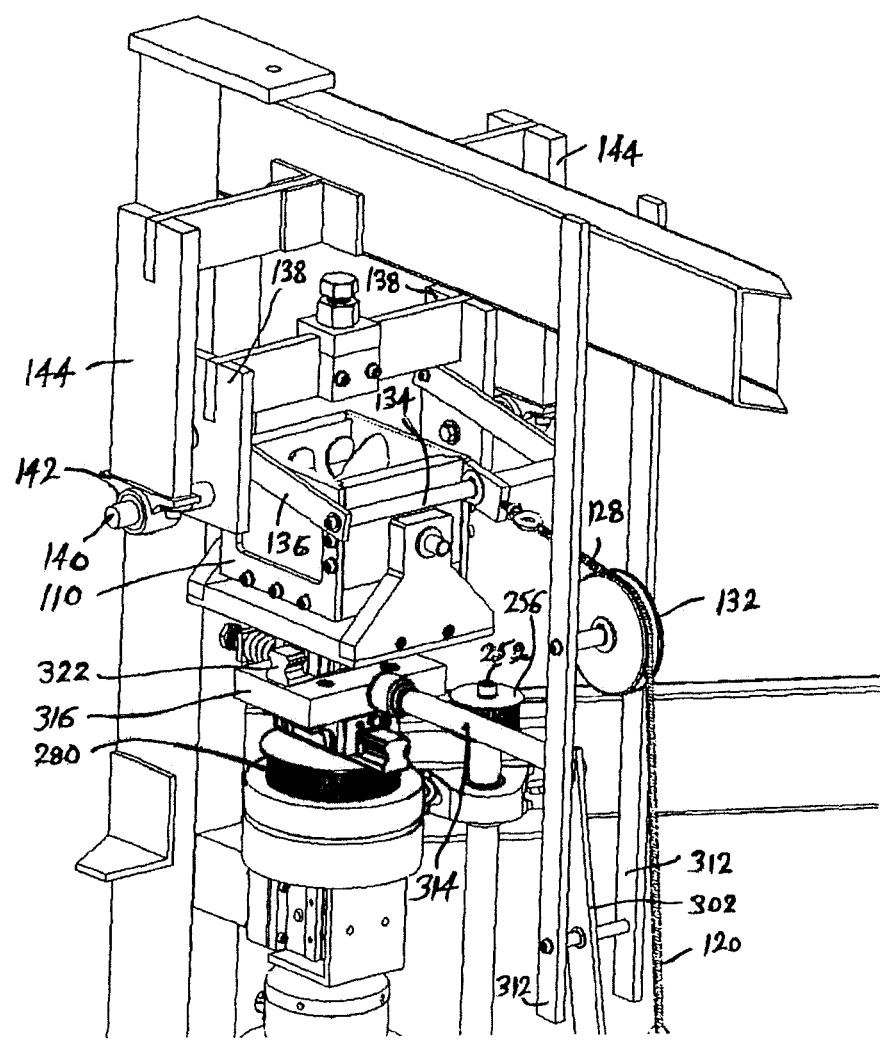
FIG. 10 is another enlarged perspective view of the test chamber.
Figure 11:
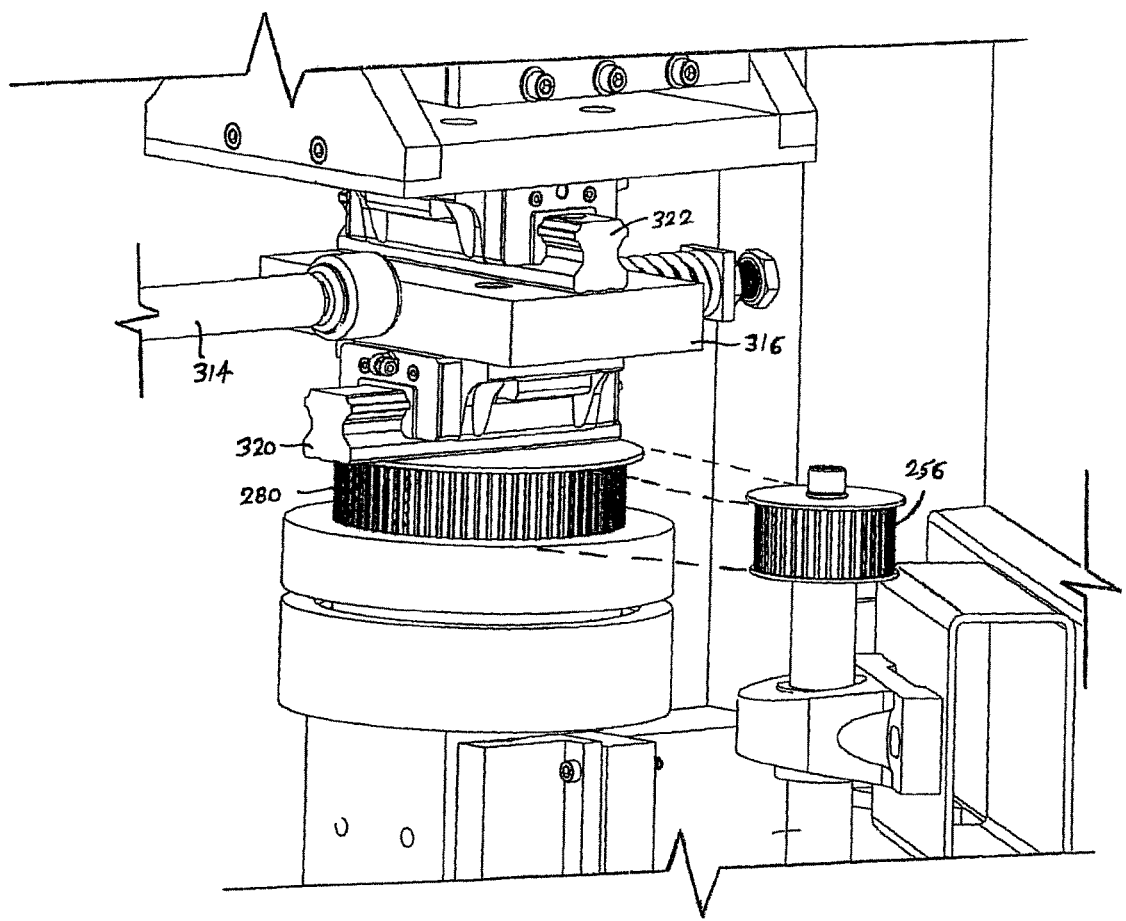
FIG. 11 is an enlarged perspective view of the rotational drive mechanism.

A third device 300 (FIGS. 2-4, 6, and 8-10) is provided for imposing a generally planar movement on the test chamber and associated specimen. This generally planar movement is also referred to as linear translation (X). The third device 300 includes an elongated arm 302 that is secured at a first or lower end to a follower 304 that cooperates with the inner profile 210 of the second cam 204 (FIGS. 3 and 6). A second or upper end of the elongated arm 302 is mounted on a pivot rod 310 that is horizontally arranged between support arms 312 extending downwardly from the frame 102. These support arms 312 in the preferred arrangement are the same arms that support the pulley 132 associated with the first device, although it will be appreciated that this need not necessarily be the case. The elongated arm 302 extends past the pivot rod 310 and is pivotally joined to one end of push member 314. An opposite end of the push member 314 engages planar block 316. Movement of the block 316 is constrained by a key and keyway arrangement 320 (FIGS. 8-10) in one direction. The key/keyway arrangement 320 provides for movement only in the X direction. This assembly 320 is also interposed between the driven gear 280 of the second drive and the test chamber 110.

The restoring member 330 (FIGS. 6 and 8) associated with the third device includes a spring 332 that extends between the frame 102 and the planar block 316. Thus the planar block 316 and push member 314 are urged away from the frame when the follower 304 moves radially outward. The mechanical details of a third mechanism that also achieves the same function may differ from that shown and described in the illustrated embodiment; however, the mechanical nature of the third mechanism is advantageously robust, reliable, accurate, inexpensive, etc. and easily synchronized with the other motion producing devices.

A fourth device or mechanism 350 is operatively connected to the test chamber 110 to impose a dynamic, compressive load force on the associated specimen ($F_z$). More particularly, the fourth device 350 (FIGS. 2 3, 6, and 7) includes a force transmitting rod 352 secured to a follower 354 at a first or lower end, and to a load cell 356 at a second or upper end. The follower 354 includes a roller 358 (FIG. 7) that is urged against the outer profile 208 of the first cam 202. The follower 354 further includes an inclined plane 360 having an angled surface 362 that is operatively engaged by a roller 364. As the inclined plane 360 moves inwardly and outwardly in a generally radial direction, the angled face 362 moves the force transmitting rod 352 upwardly and downwardly in the vertical direction. The vertical force imposed by rod 352 as a result of the inclined plane arrangement is monitored by the load cell 356. In addition, one or more springs 370 are collectively used as the restoring member for urging the fourth follower 354 against the outer profile 208 of the first cam 202. In this manner, the profile 208 of the outer cam profile of the first cam is transmitted into vertical motion or a load ($F_z$) on the test specimen 112.

A preload can also be applied to the test specimen through the fourth device. For example, the force of one or more springs 370 are effective at providing a preload transmitted through the load cell to the test chamber. In addition, the mechanical details of a fourth mechanism that also achieves the same function may differ from that shown and described in the illustrated embodiment; however, the mechanical nature of the fourth mechanism is advantageously robust, reliable, accurate, inexpensive, etc. and easily synchronized with the other motion producing devices. For example, a scissors-type mechanism may be employed that produces substantial vertical motion or force in response to radial movement dictated by the outer profile 208 of the second cam 202. Similarly, a rack and gear assembly can effectively translate radial movement of the cam outer profile 208 into vertical motion that applies a compressive force on the test specimen.

As will be appreciated, the drive mechanism 200 defined in part by cams 202, 204 is driven by a motor (not shown). The cams are rotated about a common axis and in unison. By forming the cams 202, 204 as generally annular members, radially inner and outer surfaces of each of the cams can be used as cam profiles 206, 208 and 210, 212 that operatively engage followers associated with the separate mechanical devices. Specifically, as a result, the first device creates a rotation about one of the axes, the second device imposes a rotation about one of the axes orthogonal to the first, the third device provides linear translation on the specimen along one of the axes, and a fourth device imposes a dynamic, compressive force on the specimen. Each of the first, second, third, and fourth devices includes a corresponding restoring member that is configured in a unique manner to the first, second, third, and fourth followers, respectively, to urge the followers against one of the profile surfaces of the first and second cams.

Figure 12:
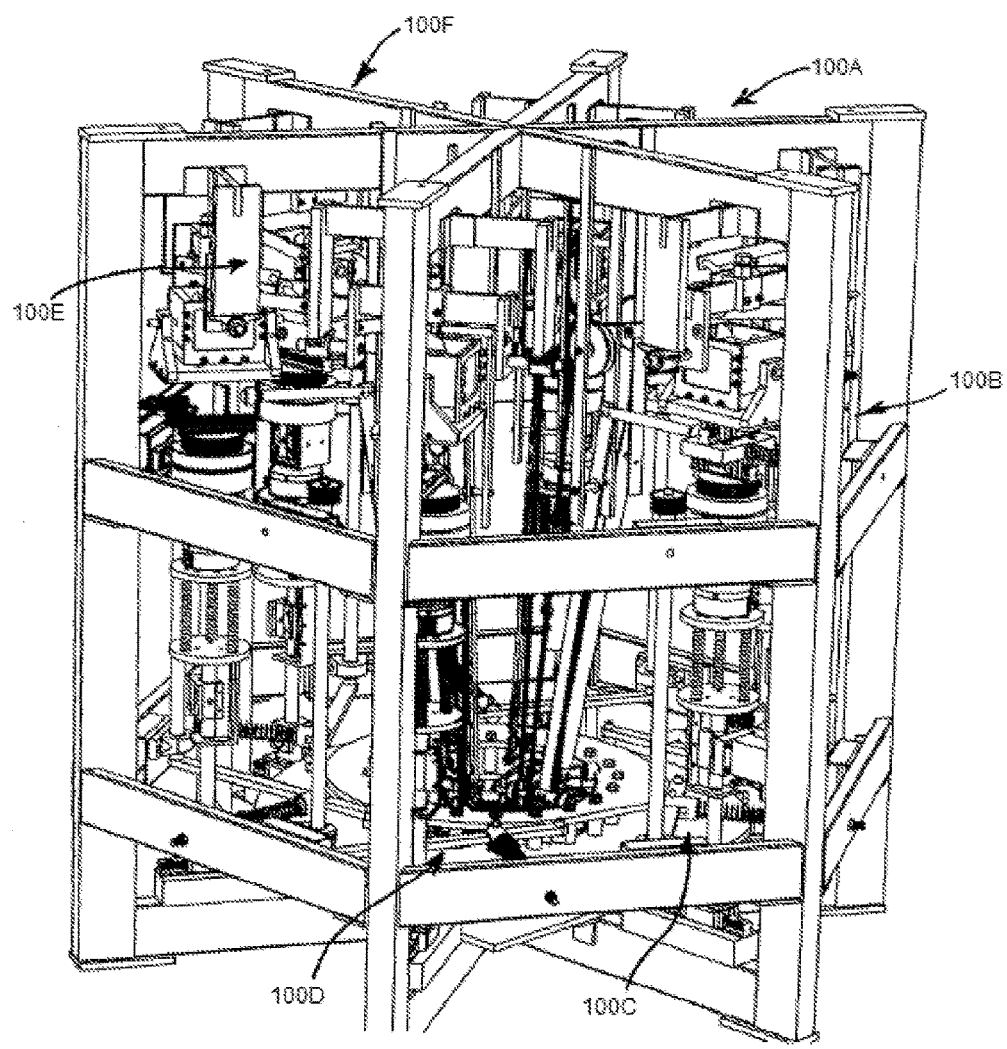
FIG. 12 is a perspective view of a system incorporating individual testing apparatus.
Figure 13:
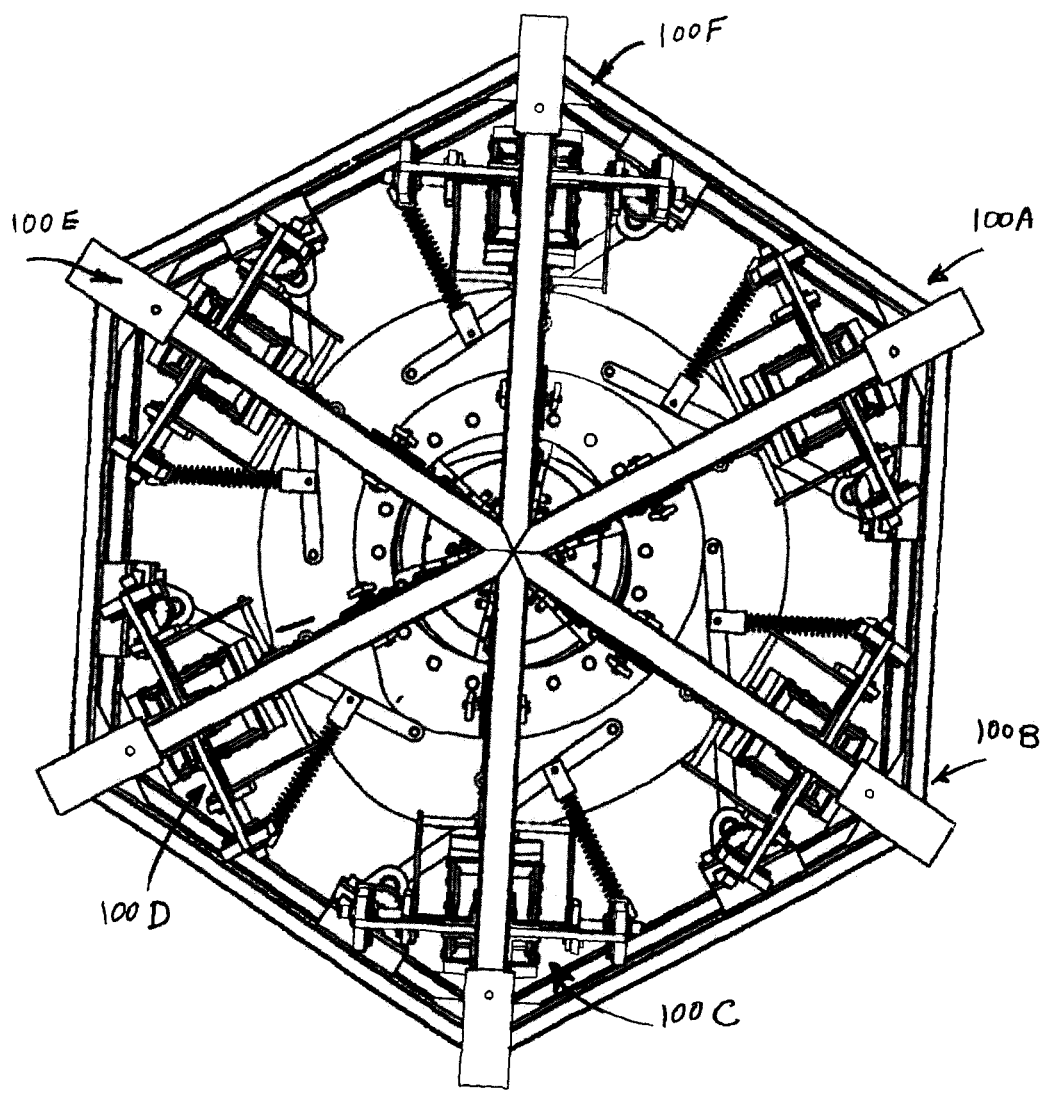
FIG. 13 is a top plan view of the system of FIG. 12.

FIGS. 12 and 13 illustrate that one of these testing apparatus can be replicated or duplicated and assembled into a system that includes a cooperating group of testing apparatus. Shown here are six separate testing apparatus labeled 100A through 100F. Each mechanism is mounted to be 60° out of phase with the next adjacent testing apparatus. Advantageously, each testing apparatus operates off the same drive mechanism, namely the first and second cams 202, 204. The structure and operation of each testing apparatus is identical to the other so that one test assembly can simultaneously test six separate specimens. The design of the profile surfaces of the respective cams assures that each testing apparatus is simultaneously undergoing the same four actions ($M_y$, $M_z$, $F_x$, and $F_z$) provided by the first, second, third, and fourth devices as described above. In other words, each of the four devices associated with one testing apparatus are coordinated or synchronized with one another, and in addition all of the four devices in each of the six testing apparatus are likewise coordinated or synchronized with the four devices of the other testing apparatus in the test system.

A modified embodiment is illustrated in FIGS. 14-19. The overall system concept is the same, i.e., a testing apparatus for an orthopaedic specimen that employs three kinematic motions and a dynamic force along the three axes of an orthogonal coordinate system which is fixed in space with its origin located within the specimen. In an attempt to simplify the above-described apparatus, the motion cams are converted to track-based cam followers. This removes the necessity for a restoring spring mechanism, thus simplifying the overall structure. In addition, the new apparatus provides for sequential application of loads/motions to each specimen. Since multiple specimens are incorporated into the test apparatus, this sequential application offers efficacy of power consumption and durability.

Further, the load/motion profiles are modified and also made to be individually adjustable. A specific cam/follower is assigned to each specimen. Further, a mechanical amplifier could be assigned to each specimen to allow for individual adjustment of one relative to the others. Still further, an initial start position can be assigned to each specimen. By modifying the displacement input profiles, force profiles are created in essentially a force driven system that accounts for soft tissue constraints. For example, and without being a limitation, the mechanism could be adapted for anterior/posterior shear, internal/external torque, and flexion/extension torque.

Yet another modification is the addition of an in-line soak control mechanism. The additional specimen serves as a baseline or control for comparison with the other specimens being tested with the same apparatus. Specifically, the specimen is typically a polymer component. As the specimen undergoes testing and is subjected to the kinematic motions, the polymer component wears, some debris is generated, and at least some of the debris is potentially washed away. Therefore, the polymer component is initially weighed, and if too much debris is generated once the testing is complete, then the specimen potentially would fail the test protocol. Therefore, it is important to determine an accurate weight of the specimen. It is also known that during the test procedure the polymer can absorb fluid from the fluid environment in which it is immersed. If the polymer absorbs fluid that is not properly accounted for, then a "false" weight may be attributed to the polymer. Therefore, adding a control specimen can be helpful.

It is desirable that the control specimen be subjected to only the vertical loading and not the kinematic motions which potentially generate the debris. As a result, the specimen is "soaked" in line with an actual test specimen but is preferably not subject to the first, second, and third kinematic motions, e.g., no anterior/posterior motion, no flexion motion, and no tibial rotation; rather, the in-line soak control specimen is only subjected to vertical loading. By situating the control soak specimen in-line, it is important that the associated fixture not create additional resistive force against the Z force (vertical load force) so that the proper load force is conveyed to the actual test specimen.

Figure 14:
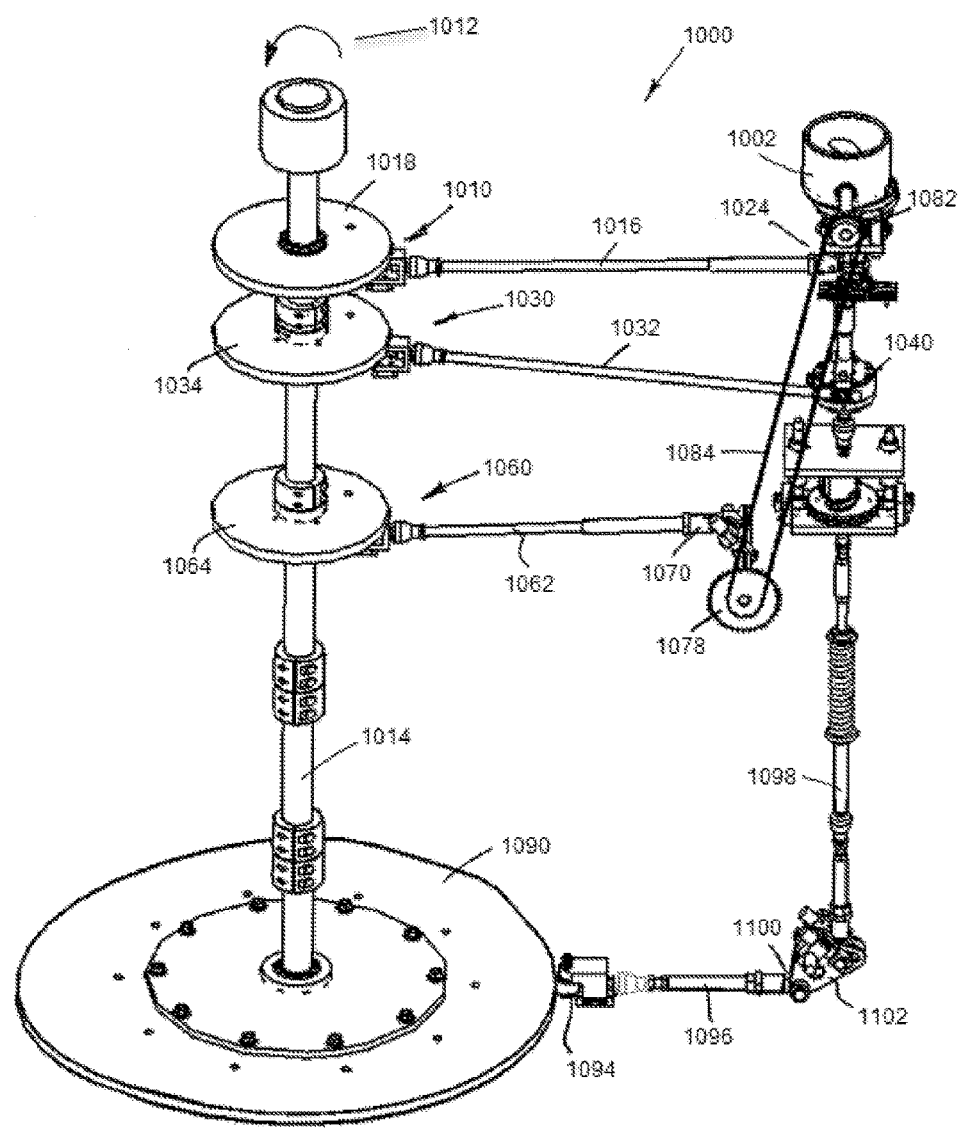
FIG. 14 is a top perspective view of a modified testing apparatus.
Figure 15:
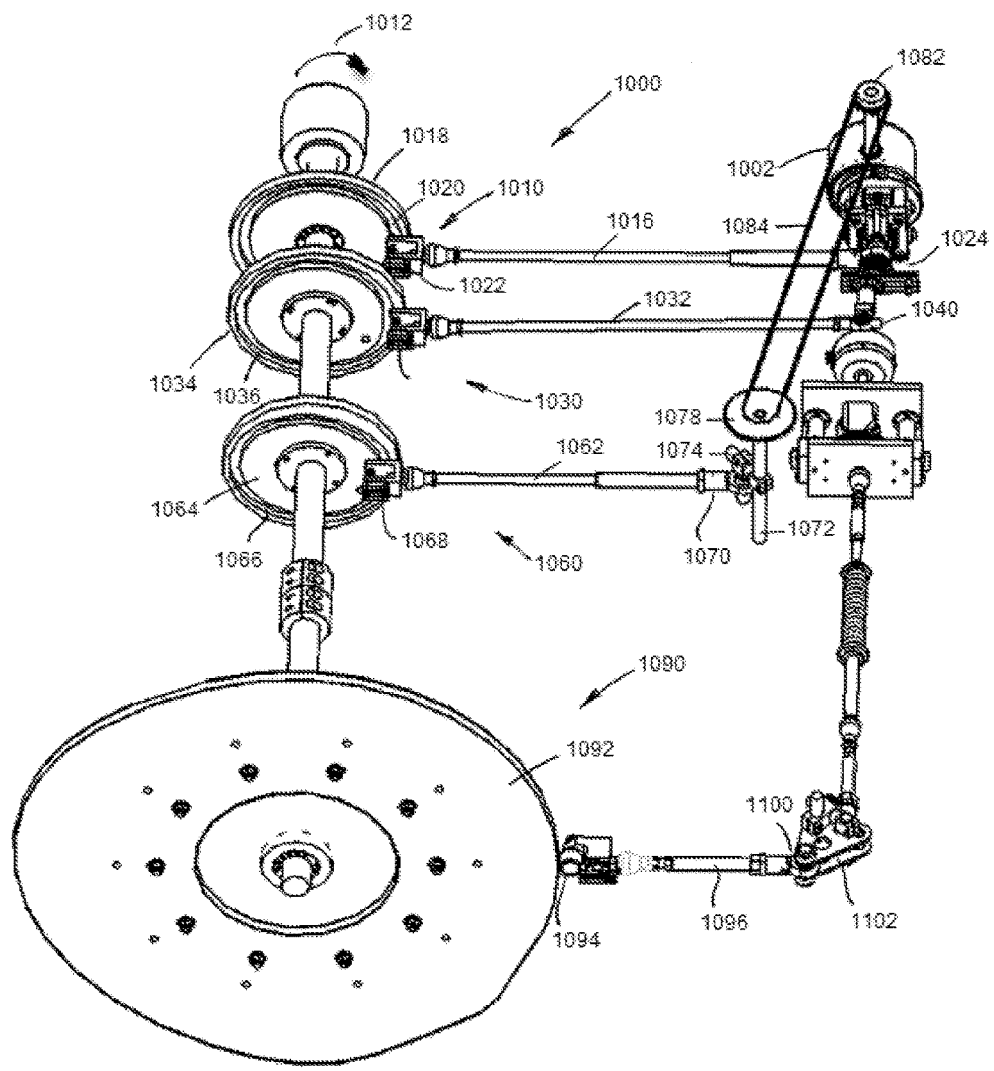
FIG. 15 is a bottom perspective view of the modified testing apparatus of FIG. 14.

FIGS. 14 and 15 illustrate a preferred arrangement of the modified system 1000 that imposes three kinematic motions and a dynamic force on a test specimen (not shown) received within a test chamber 1002. The first device or mechanism 1010 converts rotational driving force 1012 of shaft 1014 into translational movement of elongated member 1016. Particularly, a first motion cam 1018 includes a track 1020, preferably located on an undersurface thereof (FIG. 15). Locating the track 1020 on the undersurface of the cam 1018 limits the potential for any material to be inadvertently trapped in the track and potentially interfere with operation of the first mechanism 1010. The track 1020 receives a follower 1022 provided at a first end of the elongated, translational member 1016. Because the follower 1022 is received in the track 1020, movement of the follower is positively constrained by the track and eliminates the need for a restoring force (e.g., a restoring spring that might otherwise be required in connection with the follower tracking an inner or outer perimeter of a cam surface of the type shown and described in connection with the earlier embodiment). A second end 1024 of the elongated translational member 1016 is operatively connected to the test specimen contained within the test chamber 1002 to provide a first kinematic motion.

Adjustment of the first mechanism 1010 is easily achieved, for example, by altering the length of the elongated translational member 1016. Thus, there may be instances where adjustment or alteration of the first kinematic motion is desired, and thus this particular test specimen and this particular kinematic motion may be adjusted/altered without impacting the remaining test specimens or other kinematic motions or dynamic force. For example, the elongated translational member 1016 may be comprised of a pair of concentric tubes, one received inside the other, or a turnbuckle assembly, or still another structure that includes adjustment features whereby the overall length of the translational member may be selectively extended or retracted. Alternatively, the interconnection of the translational member 1016 with the second end 1024 may be changed to vary the stroke or pivot that converts the translational movement of the elongated member into a desired motion imposed on the test specimen.

A second device or mechanism 1030 converts rotational driving force 1012 provided by the shaft 1014 into translational movement of elongated translational member 1032. Particularly, a second motion cam 1034 includes a track 1036, again preferably on an undersurface thereof. The track 1036 receives a follower 1038 provided at a first end of the elongated translational member 1032. Because the follower 1038 is received in the track 1036, movement of the follower is positively constrained by the track and eliminates the need for a restoring force to urge the follower against the path of the track. A second end 1040 of the elongated translational member 1032 is operatively connected to the test specimen housed within the test chamber 1002 to provide a second kinematic motion.

Adjustment of the second mechanism 1030 is easily achieved, for example, by altering the length of the elongated translational member 1032 in a manner similar to that associated with the first elongated translational member 1016, or interconnection of the translational member 1032 with the second end 1040 may be changed to vary the stroke or pivot that converts the translational movement of the elongated member into a desired motion imposed on the test specimen. Thus, there may be instances where adjustment or alteration of the second kinematic motion is desired and as a result this particular test specimen, and this particular kinematic motion, may be adjusted/altered without impacting the remaining test specimens of the system or other kinematic motions or dynamic forces relating to this particular test specimen or the other test specimens in the system.

A third device or mechanism 1060 similarly converts rotational driving force 1012 provided by the shaft 1014 into translational movement of elongated translational member 1062. Particularly, a third motion cam 1064 includes a track 1066 on an undersurface of the cam for the same beneficial reasons noted above. The track 1066 receives a follower 1068 provided at a first end of the elongated translational member 1062. Because the follower 1068 is received in the track 1066, movement of the follower is positively constrained by the track and eliminates the need for a restoring force. A second end 1070 of the elongated translational member 1066 is operatively connected to the test specimen housed within the test chamber 1002 to provide a third kinematic motion.

Adjustment of the third mechanism 1060 is easily achieved, for example, by altering the length of the elongated translational member 1062. Thus, there may be instances where adjustment or alteration of the third kinematic motion is desired, and thus this particular test specimen, and this particular kinematic motion, may be adjusted/altered without impacting the remaining test specimens of the system or other kinematic motions or dynamic forces.

Figure 16:
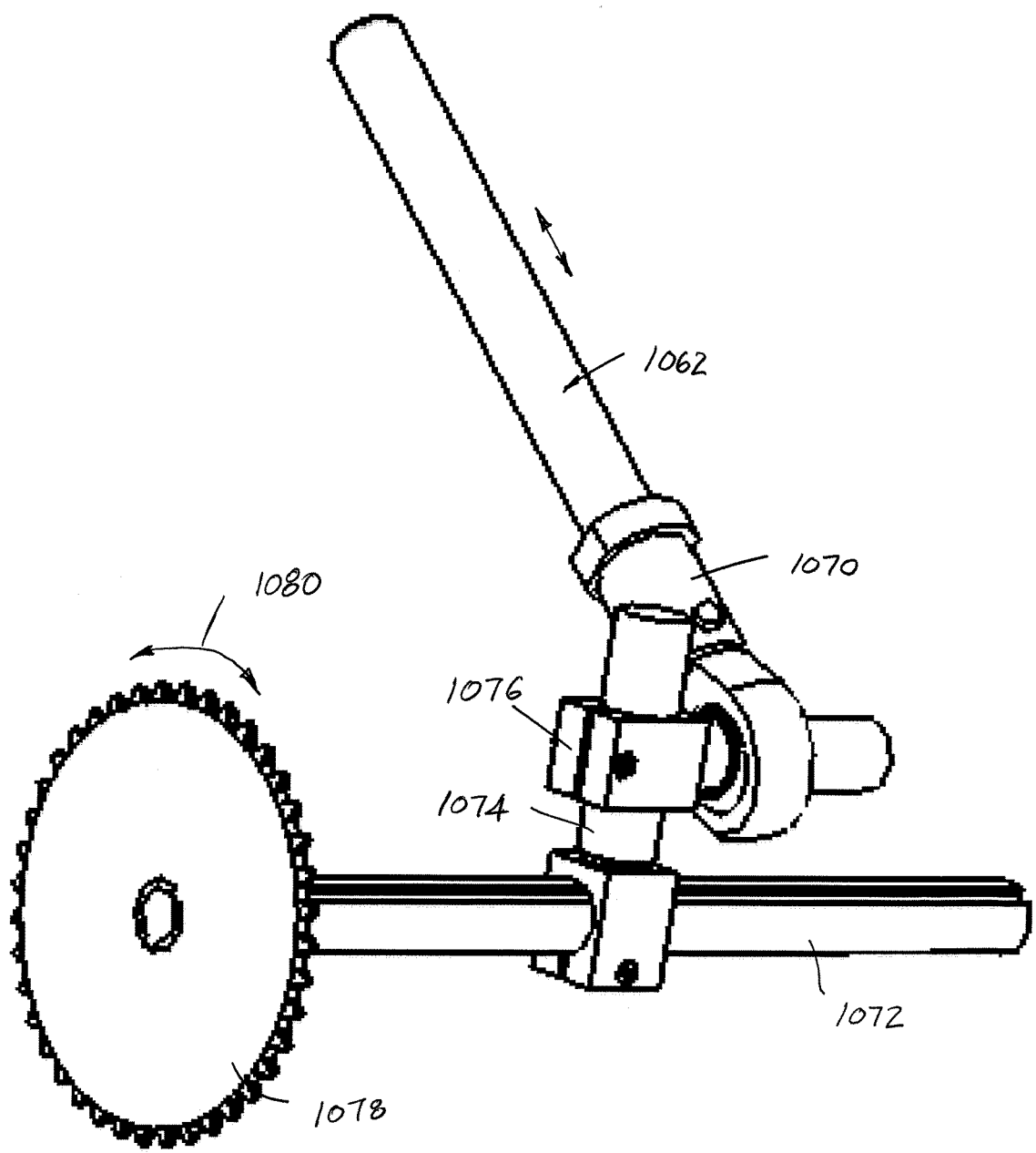
FIG. 16 is an enlarged perspective view of an adjustment linkage.

As is further evident in FIG. 16, the second end 1070 of the elongated translational member 1062 imparts selective rotation (clockwise and counterclockwise) of shaft 1072 via coupling member 1074. The point of attachment 1076 of the elongated translational member 1062 with the coupling member 1074 may be selectively altered and determines the extent of angular movement or rotation of the gear 1078 that is mounted to the shaft 1072. Thus, the further that the point of attachment 1076 is positioned away from shaft 1072 imparts a greater angular or arcuate movement of the gear 178 as referenced 1080. Simply modifying the location of this point of attachment 1076 allows for an easy adjustment of the third mechanism 1060, it being understood that the second gear 1082 associated with the test chamber 1002 is rotated in response to movement of the continuous drive member 1084 (belt or chain) to impart the third kinematic motion to the test specimen. Of course alternative mechanical arrangements for adjusting the third kinematic motion may be used without departing from the scope and intent of the present disclosure.

Figure 17:
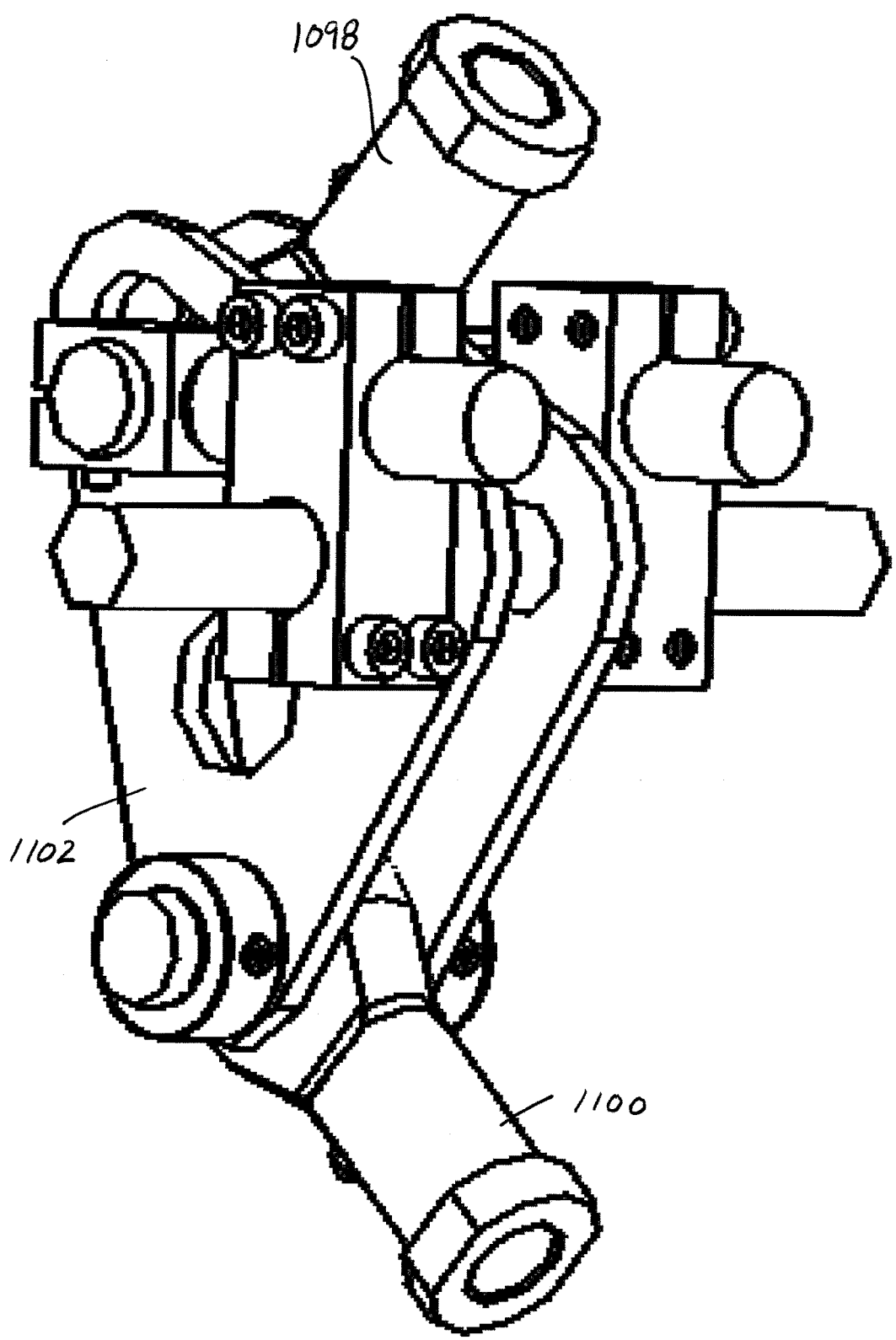
FIG. 17 is a perspective view of an adjustment mechanism

As is further illustrated in FIGS. 14 and 15 (and also with reference to FIG. 17), the fourth action imparted on the test specimen includes a mechanism 1090 having a cam 1092 and a follower 1094 disposed at one end of an elongated member 1096. As shown, the follower 1094 engages the outer perimeter of cam 1092 so that a restoring force (e.g. spring) may be required to urge the follower against the outer perimeter of the cam. Selective extension and retraction of the elongated member 1096 as a result of rotation of the cam is converted into linear movement of a second elongated member 1098 through the conversion mechanism which may also serve as a force amplifier. That is, an end 1100 of the elongated member 1096 is distal from the follower 1094 and the end is pivotally attached to member 1102 (FIG. 17). In turn, member 1102 is connected to the second elongated member 1098. The member 1102 is pivotally mounted to the system frame, and the relative position of elongated members 1096, 1098 and the pivoting member 1102 determines the linear movement of member 1098 (in a vertical direction) to impose the dynamic force on the specimen in chamber 1002. These adjustments can be easily effected by altering the relative attachment positions of the elongated members 1098, 1100 or altering the attachment points relative to the system frame in order to adjust the vertical force output through second elongated member 1098 in response to the translational movement of the first elongated 1096.

Figure 18:
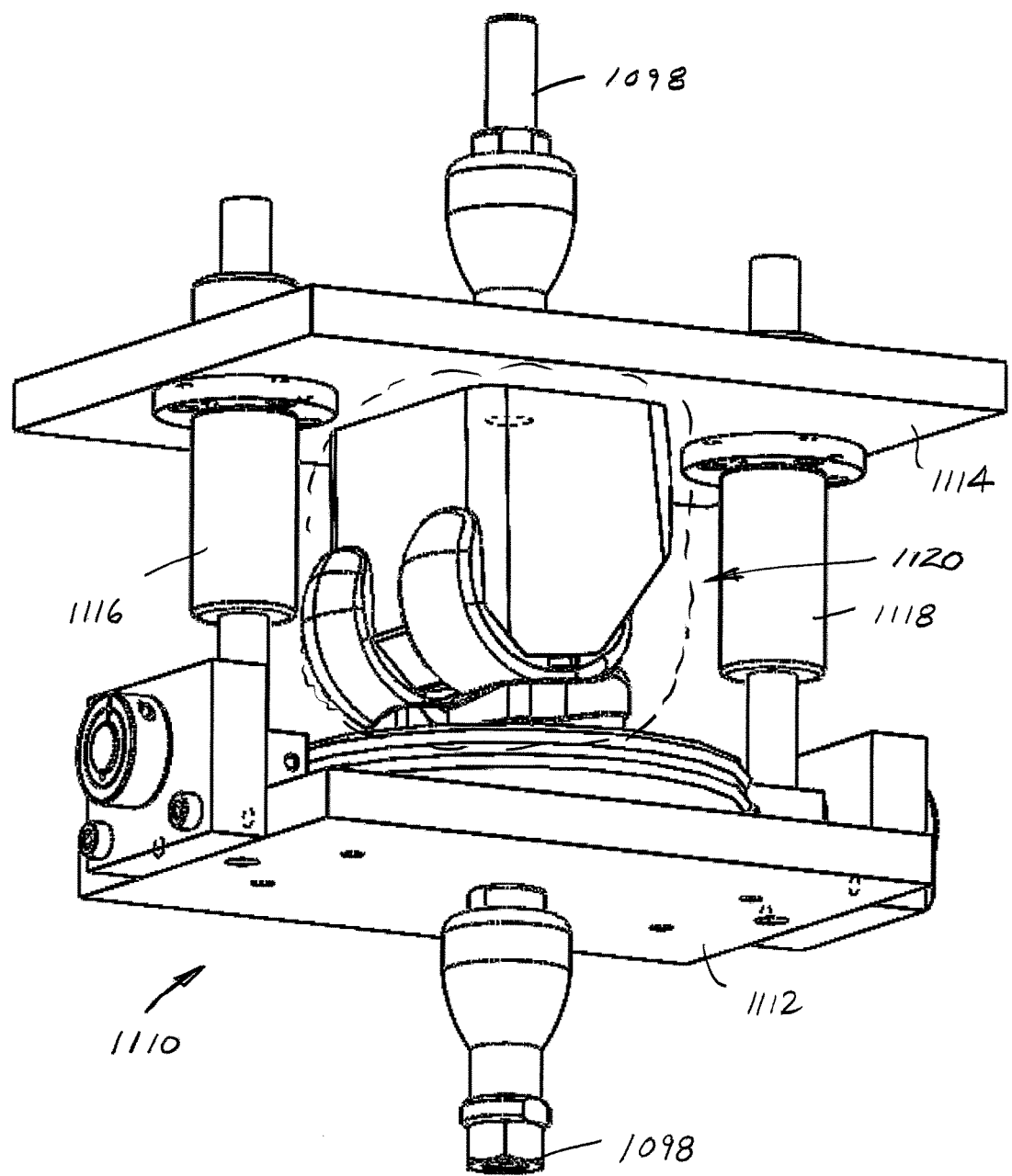
FIG. 18 is a perspective view illustrating a soak control chamber.
Figure 19:
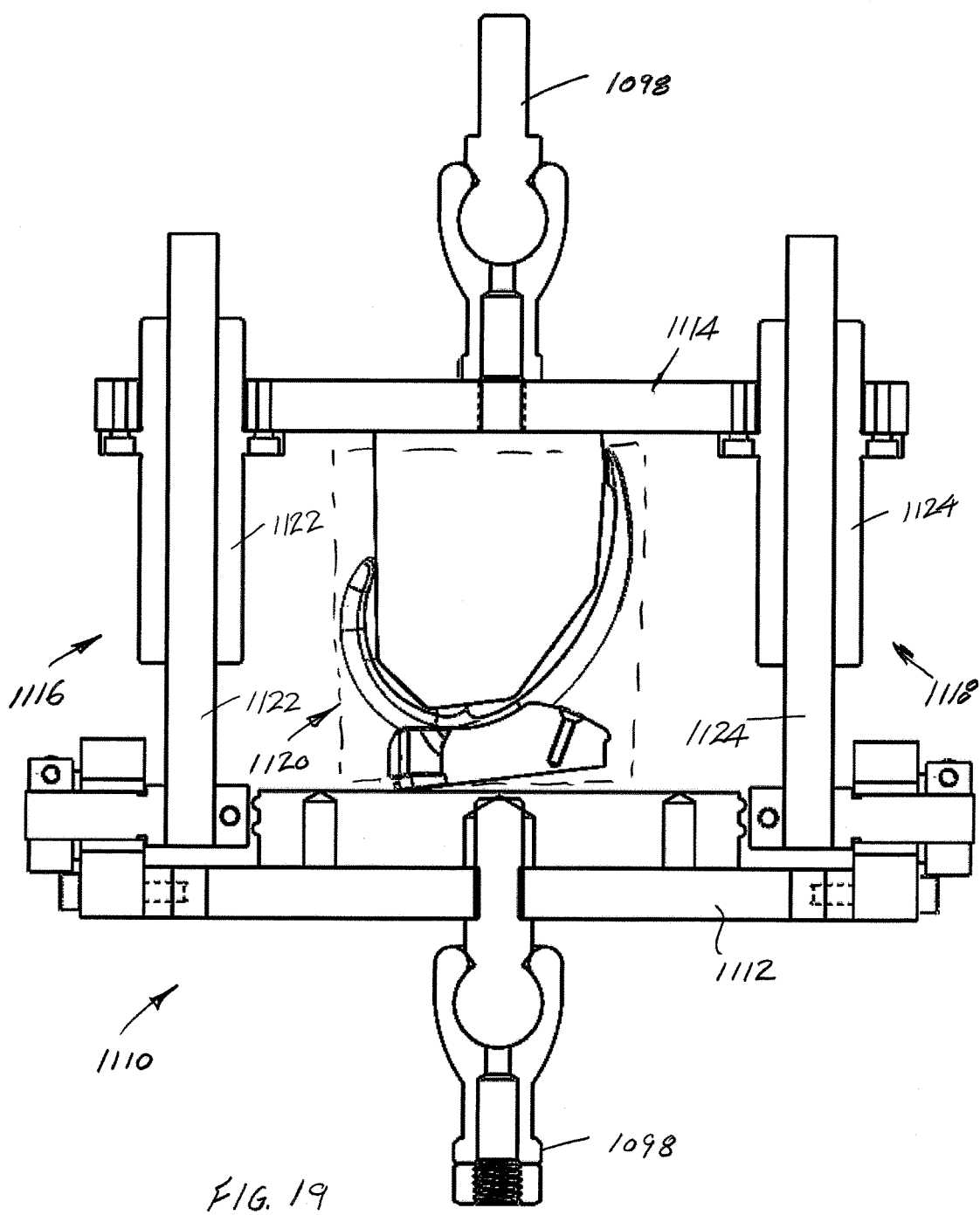
FIG. 19 is a cross-sectional view of the chamber of FIG. 18.

The dynamic force transferred through elongated member 1098 passes through an in-line soak mechanism or what is also referenced herein as an in-line soak mechanism assembly 1110 as additionally illustrated in FIGS. 18 and 19. The in-line soak control mechanism assembly 1110 includes a fixture that in one preferred arrangement has first and second spaced platforms 1112, 1114 that are interconnected, for example, by a pair of pillar assemblies 1116, 1118. The pillar assemblies 1116, 1118 are designed to transfer vertical load forces through a soak control specimen 1120, but the soak specimen is not subjected to the other three kinematic motions (e.g., anterior/posterior motion, flexion, and tibial rotation). The fixture 1112, 1114, 1116, 1118 minimizes resistive force against the vertical load forces, and allows the vertical load force to be transmitted through, so that the soak specimen 1120 serves as a control that is disposed in series with the test specimen in chamber 1002 and highly accurate comparisons can be made between the control and the test specimen. The pillar assemblies 1116, 1118 have enlarged bearing portions 1122, 1124 that receive pillars 1126, 1128, respectively, and thereby limit any forces except the vertical forces to be imposed on the soak control specimen 1120.

As a result, the first, second, and third kinematic motions (e.g., anterior/posterior motion, flexion, tibial rotation) are all conveyed to the test specimen in chamber 1002, and in addition the vertical load force is also imposed on both the soak control specimen 1120 and the test specimen in chamber 1002. Moreover, each of these motions and forces can be easily adjusted—independently or collectively—without impacting forces or motions imposed on other test specimens in the system. This allows, if desired, purposeful mal-alignment or misalignment without any impact on the specimens in other stations in the system. Such is not achievable in conventional systems (e.g. servo-hydraulic/electro-hydraulic systems available in the market). The entire system is based on a single axis (e.g. rotating shaft 1014 where various kinematic motions and forces are transferred to the test specimen in chamber 1002 and/or can be adjusted as desired). This embodiment also eliminates restoring force springs as used in the previously described embodiment. The displacement control system advantageously applies loads and therefore controls displacements in connection with the different test specimens while eliminating feedback between the different test specimens.

As a result of these modifications, at least the following specific benefits were achieved. The modified system allows for evaluation of the effects of surgical misalignment. The system allows evaluation of the effects of anatomical variation, evaluation of the effects of micro-separation, evaluation of the effects of gait speed, and advantageously allows adaptation of the system to potential changes in the standards specifications, and also easily adapts to changes in the evolution of the specimen design.

This written description uses examples to describe the disclosure, including the best mode, and also to enable any person skilled in the art to make and use the disclosure. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A testing apparatus for exposing an associated specimen to movement along multiple axes, the testing apparatus comprising:
   a first test chamber dimensioned to receive the associated specimen;
   a first device operatively connected to the first test chamber to impose a first rotational movement on the associated specimen;
   a second device operatively connected to the first test chamber to impose a second rotational movement different than the first movement on the associated specimen;
   a third device operatively connected to the first test chamber to impose a linear translation on the associated specimen;
   a fourth device operatively connected to the first test chamber to impose a dynamic force on the associated specimen;
   a drive mechanism operatively connected to the first, second, third, and fourth devices so that at least one of the first, second, third and fourth devices is driven by the drive mechanism and the at least one of the first, second, third, and fourth devices delivers a force on the test chamber; and
   an inline soak control mechanism that is dimensioned to receive an associated soak control specimen and the soak control mechanism configured so that the associated soak control specimen is not subject to the rotational movements of the first and second devices and the linear translation of the third device.

2. The testing apparatus of claim 1 wherein at least one of the first, second, third, and fourth devices includes an adjustment mechanism to modify at least one of the devices.

3. The testing apparatus of claim 2 wherein the adjustment mechanism includes a mechanical amplifier assigned to at least one of the first, second, third, and fourth devices.

4. The testing apparatus of claim 1 further comprising at least a second test chamber in addition to the first test chamber where each is operatively connected to the drive mechanism.

5. The testing apparatus of claim 4 wherein the movements and force imposed by respective ones of the devices are fixed relative to one another.

6. The testing apparatus of claim 5 wherein the drive mechanism includes separate tracks that receive respective drive members.

7. The testing apparatus of claim 1 wherein each device is operatively associated with a separate track of the drive mechanism.

8. The testing apparatus of claim 1 wherein the first device is configured to rotate the associated specimen about one of the axes of an orthogonal coordinate system fixed in space, the second device is configured to rotate the associated specimen about a second axis of the said coordinate system, the third device is configured to apply a linear translation along the third axis of the said coordinate system to the associated specimen, and the fourth device is configured to impose a periodic force on the associated specimen.

9. A testing apparatus for exposing an associated specimen to movement along multiple axes, the testing apparatus comprising:
a first test chamber dimensioned to receive the associated specimen;
a first device operatively connected to the first test chamber to impose a first, rotational movement on the associated specimen;
a second device operatively connected to the first test chamber to impose a second, rotational movement different than the first movement on the associated specimen;
a third device operatively connected to the first test chamber to impose a linear translation on the associated specimen;
a fourth device operatively connected to the first test chamber to impose a dynamic force on the associated specimen;
a drive mechanism operatively connected to the first, second, third, and fourth devices so that at least one of the first, second, third and fourth devices is driven by the drive mechanism and the at least one device delivers a force on the test chamber; and
wherein the drive mechanism includes separate tracks that receive respective drive members, and each drive member is received in the corresponding track so that no restoring member is required.

10. The testing apparatus of claim 9 wherein the tracks face downwardly to reduce debris being trapped therein.

11. The testing apparatus of claim 9 further comprising an in-line soak control mechanism for the first test chamber.

12. A testing apparatus for exposing an associated specimen to movement along multiple axes, the testing apparatus comprising:
a first test chamber dimensioned to receive the associated specimen;
a first device operatively connected to the test chamber to impose a first, rotational movement on the associated specimen;
a second device operatively connected to the test chamber to impose a second, rotational movement different than the first movement on the associated specimen;
a third device operatively connected to the test chamber to impose a linear translation on the associated specimen;
a fourth device operatively connected to the test chamber to impose a dynamic force on the associated specimen;
a drive mechanism operatively connected to the first, second, third, and fourth devices so that at least one of the first, second, third and fourth devices is driven by the drive mechanism and the at least one device delivers a force on the test chamber; and
a second test chamber that includes its own first, second, third, and fourth devices operatively associated therewith and also connected to the drive mechanism, and the first, second, third, and fourth devices of the second test chamber are sequentially operated before or after the first, second, third, and fourth devices of the first test chamber.

13. The testing apparatus of claim 12 wherein.

14. The testing apparatus of claim 12 wherein at least one of the first, second, third, and fourth devices of the first test chamber operates differently than the corresponding one of the first, second, third, and fourth devices of the second test chamber.

15. The testing apparatus of claim 14 wherein the adjustment mechanism of the at least one of the first, second, third, and fourth devices of the first test chamber that is different than the corresponding one of the first, second, third, and fourth devices of the second test chamber includes at least one of:
a mechanical amplifier,
an altered start position; and
a different displacement profile.

16. A method of testing a specimen comprising:
placing a specimen in a test chamber;
imposing a force on the specimen;
providing linear translation along a first axis of a fixed orthogonal coordinate system on the specimen;
applying two rotations to the specimen along remaining, second and third orthogonal axes of the fixed coordinate system;
driving a dynamic load, linear translation, and the two rotations with a drive mechanism; and
aligning a soak control mechanism in-line with the dynamic loading.

17. The specimen testing method of claim 16 further comprising providing an adjustment mechanism in connection with one of the force imposing, linear translation, or one of the two rotations.

18. The specimen testing method of claim 16 wherein the driving step includes commonly driving the dynamic load, linear translation, and the two rotations with a drive mechanism.

19. The specimen testing method of claim 16 wherein the driving step includes using a track-based cam that receives a follower therein.

20. The specimen testing method of claim 16 further comprising placing a specimen in a second test chamber, and purposefully adjusting at least one of the first, second, third, and fourth devices of the first test chamber to be different than a corresponding one of the first, second, third, and fourth devices of the second test chamber.

* * * * *